United States Patent [19]

Baker et al.

[11] Patent Number: 4,797,416
[45] Date of Patent: Jan. 10, 1989

[54] FUNGICIDAL CARBANILATES

[75] Inventors: Don R. Baker, Orinda; Keith H. Brownell, Cupertino; Charles Kezerian, Orinda, all of Calif.

[73] Assignee: Stauffer Chemical Co., Westport, Conn.

[21] Appl. No.: 607

[22] Filed: Jan. 5, 1987

[51] Int. Cl.$^4$ ..................... C07C 155/02; A01N 47/10
[52] U.S. Cl. ..................... 514/485; 558/241
[58] Field of Search ..................... 558/241; 514/485

[56] References Cited

U.S. PATENT DOCUMENTS 3,781,327  12/1973  Teach ................................. 558/241

FOREIGN PATENT DOCUMENTS 0093604  4/1983  European Pat. Off. ............ 558/241

Primary Examiner—Mary C. Lee
Assistant Examiner—Robert C. Whittenbaugh
Attorney, Agent, or Firm—Michael J. Bradley

[57] ABSTRACT

Novel fungicidal carbanilates having the general structural formula

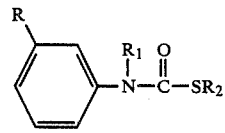

wherein R is methoxy or allyloxy; $R_1$ is selected from the group consisting of hydrogen, $C_2$–$C_4$ alkoxyalkyl and formyl; and $R_2$ is $C_1$–$C_6$ *alkyl, preferably* $C_2$–$C_3$ alkyl which are highly effective fungicides are disclosed herein.

17 Claims, No Drawings

FUNGICIDAL CARBANILATES

BACKGROUND OF THE INVENTION

Fungal growth on agriculturally important crops such as barley, rice, tomatoes, wheat, beans, roses, grapes and other agriculturally important crops can cause heavy loses in both quantity and quality of agricultural products. It is therefore extremely desirable to have means of preventing, controlling or eliminating fungal growth. Much preventative spraying with commercial fungicides is conducted to attempt to prevent the establishment and growth of fungi on agriculturally important crops.

SUMMARY OF THE INVENTION

Novel fungicidal carbanilates having the formula

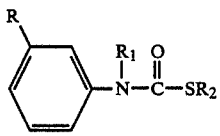

wherein R is methoxy or allyloxy; $R_1$ is selected from the group consisting of hydrogen, $C_2$–$C_4$ alkoxyalkyl and formyl; and $R_2$ is $C_1$–$C_6$ alkyl, preferably $C_2$–$C_3$ alkyl, are highly effective fungicides.

The term "fungicide" is used to mean a compound which prevents, destroys or inhibits fungal growth.

DETAILED DESCRIPTION

The novel fungicidal compounds of this invention are carbanilates having the general formula

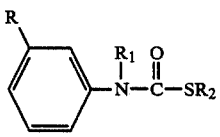

wherein R is methoxy or allyloxy; $R_1$ is selected from the group consisting of hydrogen, $C_2$–$C_4$ alkoxyalkyl and formyl; and $R_2$ is $C_1$–$C_6$ alkyl, preferably $C_2$–$C_3$ alkyl are highly effective fungicides.

By the term "alkyl" is meant both straight and branched chain alkyl.

GENERAL METHODS OF PREPARATION

The compounds of the type where $R_1$ is hydrogen are prepared by reaction of the appropriate chlorothiolformate with the appropriate aniline in an inert solvent with an acid binding agent such as pyridine, triethylamine, dimethylaniline, sodium or potassium hydroxide or carbonate.

The compounds of the type where $R_1$ is alkoxyalkyl are prepared by reaction of the compounds described above where $R_1$ is hydrogen with an alkoxyalkyl halide in the presence of an appropriate acid binding agent such as sodium hydride in an inert solvent such as ether or tetrahydrofuran.

The compounds of the type where $R_1$ is formyl are prepared by the reaction of the appropriate chlorothiolformate with an N-silyl formanilide in an inert solvent such as methylene chloride, chloroform, benzene or toluene or the like at room temperature or up to approximately 60° C.

The intermediate N-silyl formanilide is prepared from the appropriate formanilide and a silyl chloride with an acid binding agent such as triethylamine in an inert solvent such as benzene.

EXAMPLE 1

Preparation of S-Ethyl 3-allyloxy thiolcarbanilate

Ethyl chlorothiolformate (4.4 ml, 0.042 mole) was added over a period of two minutes to a solution of 3-allyloxyaniline (6.2 g, 0.0416 mole), methylene chloride (100 ml) and piperidine (4.0 ml, 0.05 mole). The temperature was maintained at 20°–25° C. with cooling. The resulting solution was allowed to stand overnight and then washed with water (100 ml), 5% hydrochloric acid solution (50 ml) and water (100 ml). This washed solution was dried over anhydrous magnesium sulfate, filtered and evaporated in vacuo to give a solid that was triturated with hexane to yield 8.8 g of the desired product, m.p. 75°–79° C.

EXAMPLE 2

Preparation of S-Ethyl 3-methoxythiolcarbanilate

A solution was prepared from 3-methoxyaniline (15.0 g, 0.17 mole), methylene chloride (100 ml) and pyridine (9.5 g, 0.17 mole). This solution was cooled to approximately 5° C. under nitrogen and to it was added ethyl chlorothiolformate (21.2 g, 0.17 mole) dropwise. The temperature was maintained at approximately 13°–15° C. The reaction was stirred overnight and washed with water, (2 times, 100 ml); dried over anhydrous magnesium sulfate, filtered and evaporated in vacuo to yield 33.5 g of the desired solid product (m.p. 39°–41° C.).

EXAMPLE 3

Preparation of N-Ethylthiocarbonyl-3methoxyformanilide

Trimethylsilyl chloride (21.6 g, 0.20 mole) was added to a solution of 3-methoxyformanilide (22 g, 0.146 mole) in benzene (200 ml) at 10° C. under a dry argon atmosphere. To this solution was added a solution of triethylamine (20 g, 0.20 mole) and benzene (50 ml) over a period of 30 minutes. The reaction mixture was stirred at room temperature for 30 minutes and filtered. The filler cake was washed with benzene (2 times with 100 ml portions). The combined filtrates were distilled and the fraction boiling at 102°–104° C. at 0.25 mm pressure collected to yield 29 g of the desired N-trimethylsilyl-3-methoxyformanilide.

The N-trimethylsilyl-3-methoxyformanilide (4.46 g, 0.02 mole) was added to a solution of ethyl chlorothiolformate (3 g) dissolved in methylene chloride (25 ml). The reaction was allowed to stand overnight at room temperature and evaporated in vacuo at 45° C. to give a 5.2 g residue. This was washed at 0° C. with hexane (100 ml) by decantation to yield 3.5 g of the desired product as a clear syrup, that solidifed and had a melting point of 42°–45° C.

EXAMPLE 4

Preparation of S-Ethyl-N-ethoxymethyl-3-allyloxythiolcarbaniliate

The product of Example 1 (3.6 g, 0.015 mole) was dissolved in dry tetrahydrofuran (50 ml) and to this solution was added sodium hydride (0.38 g, 0.016 mole)

under a dry nitrogen atmosphere with stirring for one hour. The reaction was exothermic and hydrogen gas evolved. To this solution was added chloromethyl ethyl ether (1.38 ml, 0.015 mole) and the resulting reaction was exothermic to 36° C. This mixture was stirred for 2 hours until the apparent pH of the reaction dropped to pH 6. The reaction was diluted with ether (100 ml) and methanol (5 ml), washed with water (3×100 ml); dried over anhydrous magnesium sulfate and evaporated in vacuo to give 3.9 g of the desired product as an oil.

pound to be tested is diluted with a 50/50 acetone/water solution to produce concentrations decreasing from 750 ppm. Twelve ml of test solution are sprayed onto the wheat plants with an atomizing sprayer.

A suspension of *Puccinia recondita* urediniospores is prepared by vacuuming spores from wheat leaves with uredinia pustues and suspending 10⁵ spores/ml in deionized water plus 0.5% Tween ®20. Plants are inoculated 24 hours after treatment by spraying with the spore suspension to runoff, allowing it to dry on the leaves,

TABLE I $$\text{Ar}-\underset{R_1}{\underset{|}{N}}-\underset{\underset{\|}{O}}{C}-SR_2$$
(with R on phenyl ring)

| Cmpd. No. | R | $R_1$ | $R_2$ | $n_D^{30}$ or melting point °C. |
|---|---|---|---|---|
| 1 | —OCH₂—CH=CH₂ | —H | —C₂H₅ | 75.0–79.0 |
| 2 | —OCH₂—CH=CH₂ | —H | —CH(CH₃)₂ | 34.0–36.0 |
| 3 | —OCH₂—CH=CH₂ | —CH₂OC₂H₅ | —C₂H₅ | brown oil |
| 4 | —OCH₂—CH=CH₂ | —CH₂OC₂H₅ | —CH(CH₃)₂ | brown oil |
| 5 | —OCH₃ | —CH₂OC₂H₅ | —C₂H₅ | 1.5452 |
| 6 | —OCH₃ | —CH(=O) | —C₂H₅ | 42.0–45.0 |
| 7 | —OCH₃ | —CH(=O) | —CH₃ | 57.0–59.0 |
| 8 | —OCH₃ | —CH(=O) | —C₃H₇ | 41.0–43.0 |
| 9 | —OCH₃ | —CH(=O) | —C₄H₉ | 1.5680 |
| 10 | —OCH₃ | —H | —C₂H₅ | 39.0–41.0 |

EXAMPLE 5

Preventative Spray Evaluation Procedures

Barley Powdery Mildew (BPM)

Northrup King Sunbar 401 barley seed is planted (12 seeds/2" pot) in a sandy-loam soil seven days prior to testing. The test compound is diluted in a 50/50 acetone/water solution to produce concentratons decreasing from 750 ppm (parts per million). Twelve ml of test solution are sprayed onto the barley plants with atomizing sprayers.

Twenty-four hours later, test plants are placed in an inoculation box equipped with a circulating fan. Barley plants with heavily sporulating *Erysiphe graminis* lesions are placed in front of the fan to dislodge and distribute the spores. After two minutes the fan is shut off and the chamber is left closed five minutes for the spores to settle. Inoculated plants are then placed on an automatic sub-irrigation greenhouse bench.

Results are recorded seven days following inoculation as percent disease control based on the percent reduction in lesion area as compared to the untreated control plants. Compound concentrations which provide 90% disease control (EC 90) are determined from dosage/dilution curves.

Leaf Rust (LR)

Seven seeds of Anza wheat are planted in 2" pots in a sandy-loam soil 12 days prior to testing. The comrespraying to runoff, and then placing the plants into a dark mist chamber. Following 48 hours in the mist, plants are moved to a subirrigation greenhouse bench.

Results are recorded ten days following inoculation as percent disease control based on the percent reduction in lesion area as compared to the untreated control plants. Compound concentrations which provide 90% disease control (EC 90) are determined from dosage/dilution curves.

Rose Mold (RM)

Two white rose petals are placed in a petri dish lined with wet filter paper. The compound to be tested is diluted with a 50/50 acetone/water solution to produce concentrations decreasing from 750 ppm. One half ml of test solution is atomized onto the petals, and allowed to dry.

Inoculum is prepared by adding two 5 mm plugs from a two-week old Botrytis cinerea culture grown on Elliot's V-8 agar, to 10 ml sterile distilled water plus 0.5 ml grape juice. A 20 μl drop of this inoculum suspension is placed on each petal. Petri dishes with inoculated petals are stored in sealed plastic boxes to maintain saturated humidity.

Results are read four days following inoculation as percent reduction in necrotic area compared to the acetone/water controls. Compound concentrations which provide 90% disease control (EC 90) are determined from dosage/dilution curves.

The results are presented in Table II. The results are presented as approximate EC 90 in parts per million.

TABLE II

| Cmpd. No. | BPM | LR | RM |
|---|---|---|---|
| 1 | | | 30 |
| 2 | 250 | 750 | 50 |
| 3 | | 500 | 250 |
| 4 | | | 750 |
| 5 | | | 250 |
| 6 | | | 25 |
| 7 | | | 70 |
| 8 | | | 70 |
| 9 | | | 750 |
| 10 | | | 30 |

The compounds of this invention are particularly effective against rose mold (Botrytis) and are particularly effective as preventative foliar sprays when compared to standard commercial compounds used as Botrytis preventative sprays. Fungi on which the compounds of the present invention are particularly effective are as follows: *Botyris cinerea, Erysiphe graminis* and *Puccinia recondita*.

The compounds of the present invention are useful as fungicides and can be applied in a variety of ways at various concentrations. In practice, the compounds herein defined are formulated into fungicidal compositions, by admixture, in fungicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as granules of relatively large particle size, as wettable powders, as emulsifiable concentrates, as powdery dusts, as solutions or as any of several other known types of formulations, depending upon the desired mode of application. Preferred formulations for preventative or curative fungicidal applications are wettable powders, emulsifiable concentrates and granules. These formulations may contain as little as about 0.5% to as much as about 95% or more by weight of active ingredient. A fungicidally effective amount depends upon the nature of the disease to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the plant or soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifier concentrates are homogeneous liquid compositions which are dispersible in water or other dispersant, and may consist entirely of the active compound with a liquid or solid emusifying agent, or may also contain a liquid carrier, such as xylene, heavy aromatic naphtha, isophorone and other non-volatile organic solvents. For fungicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the fungicidal composition.

Granular formulations wherein the toxicant is carried on relatively coarse particles, are usually applied without dilution to the area in which disease control is desired. Typical carriers for granular formulations include sand, fuller's earth, bentonite clays, venmiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about of active ingredient by weight, and may also contain small amounts of a wetting, dispersing or emulsifying agent to facilitate dispersion. For application, the pastes are normally diluted and applied as a spray to the area to be treated.

| EXAMPLES OF TYPICAL FORMULATIONS | |
|---|---|
| Ingredient | Weight % |
| Oil | |
| Compound 1 | 1 |
| Oil solvent-heavy aromatic naphtha | 99 |
| Total | 100 |
| Emulsifiable Concentrate | |
| Compound 2 | 50 |
| Kerosene | 45 |
| Emulsifying agent (mixture of long | 5 |

| | EXAMPLES OF TYPICAL FORMULATIONS | | | |
|---|---|---|---|---|
| | chain ethoxylated polyethers with long chain sulfonate) | | | |
| | | Total | 100 | |
| | Compound 3 | | 90 | |
| | Kerosene | | 5 | |
| | Emulsifying agent (mixture of long chain ethoxylated polyethers with long chain sulfonate) | | 5 | |
| | | Total | 100 | |
| Ingredient | | Wt. % | Wt. % | Wt. % |
| | Dusts and/or Powders | | | |
| Compound 4 | | 0.5 | 50.0 | 90.0 |
| Attapulgite Clay Powder | | 93.5 | 44.0 | 4.0 |
| Sodium lignin sulfonate | | 5.0 | 5.0 | 5.0 |
| Sodium dioctyl sulfosuccinate | | 1.0 | 1.0 | 1.0 |
| | Total | 100.0 | 100.0 | 100.0 |

Other useful formulations for fungicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages.

We claim:

1. A compound having the structural formula

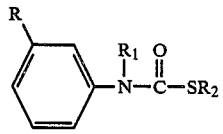

wherein R is methoxy or allyloxy; $R_1$ is selected from the group consisting of $C_2$-$C_4$ alkoxyalkyl and formyl; and $R_2$ is $C_1$-$C_6$ alkyl.

2. The compound of claim 1 wherein R is —OCH$_2$CH=CH$_2$, $R_1$ is —CH$_2$OC$_2$H$_5$ and $R_2$ is —C$_2$H$_5$.

3. The compound of claim 1 wherein R is —OCH$_2$CH=CH$_2$, $R_1$ is —CH$_2$OC$_2$H$_5$ and $R_2$ is —CH(CH$_3$)$_2$.

4. The compound of claim 1 wherein R is —OCH$_3$, $R_1$ is —CH$_2$OC$_2$H$_5$ and $R_2$ is —C$_2$H$_5$.

5. The compound of claim 1 wherein R is —OCH$_3$, $R_1$ is

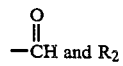

is —C$_2$H$_5$.

6. The compound of claim 1 wherein R is —OCH$_3$, $R_1$ is

is —CH$_3$.

7. The compound of claim 1 wherein R is —OCH$_3$, $R_1$ is

is —C$_3$H$_7$.

8. The compound of claim wherein R is —OCH$_3$, $R_1$

is —C$_4$H$_9$.

9. A fungicidal composition comprising a fungicidally effective amount of a compound having the structural formula

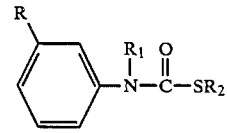

wherein R is methoxy or allyloxy; $R_1$ is selected from the group consisting of $C_2$-$C_4$ alkoxyalkyl and formyl; and $R_2$ is $C_1$-$C_6$ alkyl; and an inert diluent carrier.

10. The method of controlling fungi comprising applying to the area where control is desired, a fungicidally effective amount of a compound having the formula

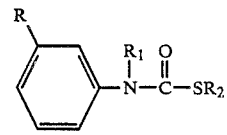

wherein R is methoxy or allyloxy; $R_1$ is selected from the group consisting of $C_2$-$C_4$ alkoxyalkyl and formyl; and $R_2$ is $C_1$-$C_6$ alkyl.

11. The method of claim 10 wherein R is —OCH$_2$CH=CH$_2$, $R_1$ is —CH$_2$OC$_2$H$_5$ and $R_2$ is —C$_2$H$_5$.

12. The method of claim 10 wherein R is —OCH$_2$CH=CH$_2$, $R_1$ is —CH$_2$OC$_2$H$_5$ and $R_2$ is —CH(CH$_3$)$_2$.

13. The method of claim 10 wherein R is —OCH$_3$, $R_1$ is —CH$_2$OC$_2$H$_5$ and $R_2$ is —C$_2$H$_5$.

14. The method of claim 10 wherein R is —OCH$_3$, $R_1$ is

is —C$_2$H$_5$.

15. The method of claim 10 wherein R is —OCH$_3$, $R_1$ is

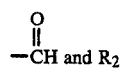
is —CH₃.
16. The method of claim 10 wherein R is —OCH₃, R₁ is
is —C₃H₇.
17. The method of claim 10 wherein R is —OCH₃, R₁ is
is —C₄H₉.
* * * * *